(12) United States Patent
Dick et al.

(10) Patent No.: US 10,463,430 B2
(45) Date of Patent: Nov. 5, 2019

(54) METHOD AND DEVICE FOR COMBINED TEMPERATURE-CONTROLLED LASER THERAPY BY MEANS OF A MULTIFUNCTIONAL THERAPY LASER

(75) Inventors: Manfred Dick, Gefell (DE); Rene Denner, Reisdorf (DE); Gerald Kunath-Fandrei, Jena (DE)

(73) Assignee: CARL SEISS MEDITEC AG, Jena (DE)

( * ) Notice: Subject to any disclaimer, the term of this patent is extended or adjusted under 35 U.S.C. 154(b) by 1663 days.

(21) Appl. No.: 14/237,899

(22) PCT Filed: Jul. 26, 2012

(86) PCT No.: PCT/EP2012/003177
§ 371 (c)(1),
(2), (4) Date: Apr. 30, 2014

(87) PCT Pub. No.: WO2013/020660
PCT Pub. Date: Feb. 14, 2013

(65) Prior Publication Data
US 2014/0243805 A1 Aug. 28, 2014

(30) Foreign Application Priority Data

Aug. 10, 2011 (DE) .......................... 10 2011 109 936

(51) Int. Cl.
*A61B 18/20* (2006.01)
*A61F 9/008* (2006.01)
(Continued)

(52) U.S. Cl.
CPC .......... *A61B 18/20* (2013.01); *A61F 9/00823* (2013.01); *A61N 5/06* (2013.01);
(Continued)

(58) Field of Classification Search
CPC ................ A61B 18/20; A61F 9/00823; A61F 2009/00863; A61N 5/06; A61N 2005/067
(Continued)

(56) References Cited

U.S. PATENT DOCUMENTS

2005/0033388 A1 2/2005 Brugger et al.
2007/0230520 A1 10/2007 Mordaunt et al.
(Continued)

FOREIGN PATENT DOCUMENTS

DE 102009016184 A1 10/2010
JP 2004518508 A 6/2004
(Continued)

OTHER PUBLICATIONS

Machine translation of WO2010112209.*
(Continued)

*Primary Examiner* — Carl H Layno
*Assistant Examiner* — Dacheng Xie
(74) *Attorney, Agent, or Firm* — Leydig, Voit & Mayer, Ltd.

(57) ABSTRACT

A laser therapy device includes a solid-state laser configured for a CW operation and including a pump source, and a controller configured to generate at least one first pulse of the laser in a first-pulse operation. The controller is configured to switch on the pump source to a pump power level S1 at least once during the first-pulse operation. A rise time E, after which the pump power level S1 of the pump source is attainable and starting from the time the pump source is switched on, is in a range of 50 ns to 350 ns.

25 Claims, 4 Drawing Sheets

Figure 1:
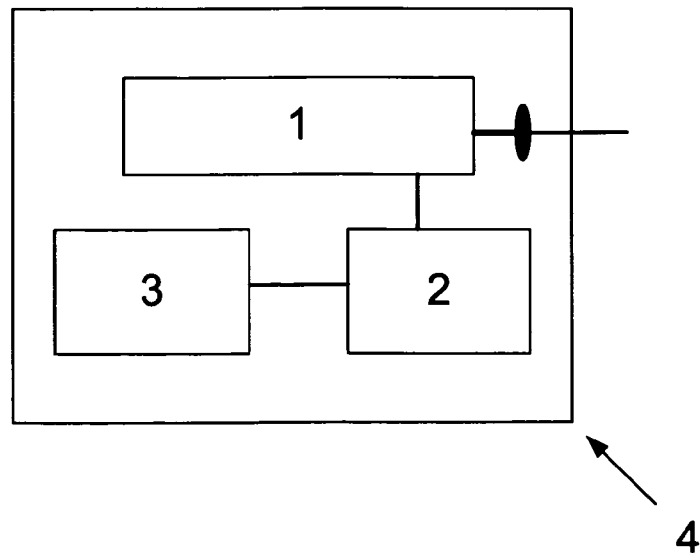

(51) Int. Cl.
*A61N 5/06* (2006.01)
*A61B 18/00* (2006.01)
*A61N 5/067* (2006.01)

(52) U.S. Cl.
CPC .............. *A61B 2018/0066* (2013.01); *A61F 2009/00863* (2013.01); *A61N 2005/067* (2013.01)

(58) Field of Classification Search
USPC .................................. 606/2–19; 607/86–94
See application file for complete search history.

(56) References Cited

U.S. PATENT DOCUMENTS

| | | | |
|---|---|---|---|
| 2008/0086118 A1 | 4/2008 | Lai et al. | |
| 2008/0262577 A1* | 10/2008 | Altshuler | A61C 1/0046 607/89 |
| 2009/0207871 A1 | 8/2009 | Koshimae et al. | |
| 2009/0245300 A1 | 10/2009 | Sun et al. | |
| 2012/0089132 A1* | 4/2012 | Dick | A61B 5/0095 606/4 |

FOREIGN PATENT DOCUMENTS

| | | |
|---|---|---|
| JP | 2006503432 A | 1/2006 |
| JP | 2011515870 A | 5/2011 |
| WO | 2007129363 A | 11/2007 |
| WO | WO 2010112209 A | 10/2010 |
| WO | WO 2010112209 A1 | 10/2010 |

OTHER PUBLICATIONS

Alsous, M.B., Q-Switch Rise Time Effect in Flash-Pumped Solid State Lasers, Law Physics, 2010, vol. 20, No. 5, pp. 1095-1100.*
Sakugawa et al, Generation of streamer discharge plasma in water by all solid-state pulsed power, Transaction of the Institute of Electrical Engineers of Japan 2006 (Year: 2006).*
Gan et al, Development on the 10 kV solid-state switch, High Power Laser and Particle Beams, Oct. 2003 (Year: 2003).*
Kalinin et al, Laser setup with the use of nonlinear optical phenomena and its application for high-temperature plasma probing, Laser Optics 2003 (Year: 2003).*
Li, et al., "Single continuous-wave mode-locked Nd:GdVO$_4$-semiconductor saturable absorber mirror laser", Optical Engineering, vol. 48, Nr. 7, Jul., 2009, pp. 074201-1-074201-3.
Dorin, The treatment of Diabetic Retinopathy (DR): Laser Surgery or Laser Therapy?, RetinaToday, vol. 6, Nr. 1, Dec. 2008, pp. 1-12.

\* cited by examiner

METHOD AND DEVICE FOR COMBINED TEMPERATURE-CONTROLLED LASER THERAPY BY MEANS OF A MULTIFUNCTIONAL THERAPY LASER

CROSS REFERENCE TO RELATED APPLICATIONS

This application is a U.S. National Phase application under 35 U.S.C. § 371 of International Application No. PCT/EP2012/003177, filed on Jul. 26, 2012, and claims benefit to German Patent Application No. DE 10 2011 109 936.4, filed on Aug. 10, 2011. The International Application was published in German on Feb. 14, 2013 as WO 2013/020660 A1 under PCT Article 21 (2).

FIELD

The invention relates to an apparatus and a method for combined temperature-controlled laser therapy by means of a multifunctional therapy laser. In particular, the invention relates to a therapy laser that has an extended range of application in comparison with existing lasers.

BACKGROUND

DE 10 2009 016 184 A1 discloses a method and an apparatus for non-invasive temperature determination on biological tissue treated with a CW treatment radiation. In that case, the laser pump source is switched on rapidly, within approximately 1-10 μs, to generate short, intensive laser pulses having a power peak of approximately 10 W, wherein the average power attained by the CW laser is approximately 2 W. These pulses are used to generate signals that can be evaluated by optoacoustic means and that are suitable for measuring the temperature of the treated tissue.

In the case of the lasers of the state of the art, the restricted range of use has been considered to be disadvantageous.

SUMMARY

In an embodiment, the present invention provides a laser therapy device including a solid-state laser configured for a CW operation and including a pump source, and a controller configured to generate at least one first pulse of the laser in a first-pulse operation. The controller is configured to switch on the pump source to a pump power level S1 at least once during the first-pulse operation. A rise time E, after which the pump power level S1 of the pump source is attainable and starting from the time the pump source is switched on, is in a range of 50 ns to 350 ns.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIG. 1 shows an overview of a laser therapy device (4) according to the invention, FIG. 2 shows a pump power (PP)-time (t) diagram of a control, according to the invention, of a pump source (2), FIG. 3 shows a laser power (PL)-time (t) diagram of first pulses according to the invention, FIG. 4 shows a laser power (PL)-time (t) diagram of pulse packets of first pulses according to the invention, FIG. 5 shows a laser power (PL)-time (t) diagram of extended first pulses according to the invention, with a shoulder characteristic resulting from holding a pump power level S2 after switch-on of the pump source to a pump power level S1, FIG. 6 shows a laser power (PL)-time (t) diagram of pulse packets of extended first pulses according to the invention, with a shoulder characteristic, FIG. 7 shows a laser power (PL)-time (t) diagram of treatment pulses according to the invention and of a treatment beam according to the invention, FIG. 8 shows a laser power (PL)-time (t) diagram of pulse packets of treatment pulses according to the invention, FIG. 9 shows a laser power (PL)-time (t) diagram of treatment pulses according to the invention without complete reduction of the pump power between the treatment pulses, FIG. 10 shows a laser power (PL)-time (t) diagram of pulse packets of treatment pulses according to the invention without complete reduction of the pump power between the treatment pulses, FIG. 11 shows a laser power (PL)-time (t) diagram of treatment pulses and measuring pulses according to the invention, FIG. 12 shows a laser power (PL)-time (t) diagram of a CW treatment beam according to the invention.

DETAILED DESCRIPTION

An aspect of the present invention is to provide a laser for a broader spectrum of application.

In the present invention provides a laser therapy device (4), comprising a laser (1) and a control means (3), wherein the laser (1) is a solid-state laser suitable for a CW operation and comprises a pump source (2), and wherein the control means (3) is designed to generate at least one first pulse of the laser (1) in a first-pulse operation, wherein, in the first-pulse operation, the pump source (2) can be switched on to a pump power level S1 at least once by the control means (3), and wherein a rise time E, after which the pump power level S1 of the pump source (2) can be attained, starting from the switch-on, lies in the range of from 5 ns to 350 ns.

This provides a laser with which, by means of special control of a continuous-wave laser (CW laser), in addition to the continuous operation of the CW laser, it is possible to generate short, intensive pulses that, despite the low CW laser power, or low nominal power of the CW laser, have a laser pulse peak power that is many times greater, such that these pulses can be used for therapy methods that hitherto could not be performed by means of a CW laser, such as, for example, selective photothermolysis of the retina and, at the same time, the CW laser can be used for therapy methods such as, for example, photocoagulation, hyperthermia and biostimulation in the eye. It has been discovered, unexpectedly, that, by switching on the pump source yet more rapidly, as compared with the state of the art, it is possible to generate first pulses having pulse peak powers of approximately 35 W, wherein the CW power is, for example, only approximately 2 W. The pulse peak power obtained is thus more than 10 times greater than the CW laser power. The resultant first pulses have a FWHM (full width at half maximum; half-value width) of approximately 0.25 µs and, in the example of a CW laser having a CW laser power of 2 W, attain a pulse energy of up to 20 P. Such pulses are suitable, for example, for biostimulation of the RPE cells and for photodisruption of organic tissue following selective photothermolysis. The laser therapy device can therefore be used both for a CW operation for photocoagulation with temperature control, and in therapeutically effective single-pulse operation.

The laser is preferably a CW laser, such as that used for photocoagulation. Preferably, it is a diode-pumped solid-state laser. The laser preferably works with wavelengths in the visible and infrared wavelength range, preferably from 400 to 1000 nm, particularly preferably from 510 to 810 nm, and specifically 532 nm, 561 nm, 577 nm, 659 nm. It is preferably a primarily continuously emitting therapy laser. It is preferably an optically excited laser, whose gain (active) medium consists of a crystalline or glass-type (amorphous) solid. This so-called host material or host crystal contains a certain concentration (doping) of the laser-active ions. The active medium of the laser is preferably able to store the energy delivered during the pumping process for an intermediate period, e.g. in the form of a population inversion, and to deliver it, substantially in a single pulse, upon a starting operation of the light field in the laser resonator. Such a medium is, for example, a solid-state laser medium, whose energy storage time (terms also used in connection with this are fluorescence lifetime or upper-state lifetime) typically lies in the range of from 50 µs to 1 ms. Preferably, as active media having corresponding dopings, one or more may be selected from the following group: Nd:YAG (230-240 µs fluorescence lifetime), all crystals, neodymium:yttrium-vanadate, neodymium:yttrium-aluminium-garnet (Nd:YAG), Er:YAG, Tm:YAG, Ho:YAG Ho—Tm:YAG.

A population inversion exists when the population of the higher-energy, upper laser level involved in the laser amplification process is greater than that of the involved lower laser level. In an advantageous embodiment example, the laser is a neodymium:yttrium-vanadate solid-state laser having a wavelength of 1064 nm and having a frequency doubling of a wavelength of 532 nm. Owing to the comparatively short fluorescence lifetime, or storage time, of this laser-active medium, of approximately 100 µs, the switch-off time can be limited, in the case of modulation, to this short time period. Advantageously, a diode is provided as a pump source for the laser since, in this case, the pump source can easily be modulated through appropriate control of the diode current. Preferably, the laser is a disk laser. Since the laser material is realized in the form of a very thin disk that is cooled in the axial direction, the construction of a thermal lens is minimized. This ensures, in particular, that, in the case of time-varying control, the beam parameters of the laser emission do not vary as a result of the type, and over the duration, of the modulation, and the advantage according to the invention, of a correspondence between the measurement volume, treatment volume and first-pulse volume, is thus fully realized. In a particularly advantageous embodiment example, the laser is a diode-pumped neodymium:yttrium-vanadate disk laser with frequency doubling.

The laser is preferably suitable for a CW operation if it is normally applied for forms of therapy effected with continuous irradiation. Typical, for example, is a photocoagulation laser having a maximum CW laser power of 2 W, also up to 5 W in stronger versions, wherein, for example, a CW laser power of 100 mW-500 mW is already sufficient for photocoagulation, preferably with coagulation times of 10 ms-500 ms. According to the invention, such a laser can now also be used for other forms of therapy that require a higher peak power (e.g. cell death of the RPE caused by bubble formation as a result of selective photothermolysis).

A suitable control means is any means that can control a device in dependence on an input quantity. The controller preferably has both at least one input interface and at least one output interface. Preferably, the controller is programmable. Preferably, a hard-wired programmed controller is used, particularly preferably a stored-program controller. Preferably, the controller has a processor architecture.

The pump source is preferably at least one diode, whose radiation intensity can be controlled by means of current control and which excites the laser. The pump power of the pump source can preferably be controlled through the current and voltage. Preferably, it is possible to set individual pump power levels of the pump source; particularly preferably, these pump power levels can be selected for any pump power values. The control means can set the pump source to a particular pump power level, through a corresponding voltage and a corresponding current. For example, a laser diode (laser diodes), LED (LEDs) or gas discharge lamps may be used as a pump source. Diodes are preferred because they can be connected rapidly. The laser medium can be excited both longitudinally and transversely.

The pump power is preferably the power that is supplied to the pump source for the purpose of exciting the laser medium, e.g. in the form of current and voltage.

The laser power is preferably the power delivered by the laser in the form of photons.

The CW laser power is preferably the CW nominal power of the laser. The CW nominal power is preferably the laser power that can be delivered in a stable and constant manner in continuous operation in the minute range or longer. Particularly preferably, the CW nominal power is a power value, specified by the manufacturer, for continuous operation in, at least, the minute range.

The mean laser power is preferably the laser power that, averaged over time, is delivered by the CW laser, preferably during a pulsed operation of the CW laser, or during a quasi-continuous operation of the CW laser by the corresponding pulses. If, for example in one minute, five treatment pulses are emitted, each having a duration of 10 seconds and a laser power of 2 watts, and the laser power between the pulses is 0 watts, then, according to $$\frac{5 \cdot 10s \cdot 2W}{6 \cdot 10s} = 1.667W$$

the mean laser power is 1.667 watts.

In first-pulse operation, at least one first pulse of the laser is generated, preferably a plurality of first pulses in succession. Preferably, the control means is designed such that, before switching on the pump source to the pump power level S1, it maintains a pause of 40 µs to 2 ms, preferably of 50 µs to 1 ms, in which the radiation field present in the laser resonator disintegrates and a population inversion degenerates through spontaneous disintegration. Preferably, the length of the pause corresponds approximately to the aforementioned storage time of the active laser medium.

A first pulse is a short, intensive laser pulse having a pulse peak power that, unexpectedly, is more than ten times greater than the CW laser power and, unexpectedly, is more than three times greater than the pulse peak power of a first pulse, known from DE 10 2009 016 184 A1, used for temperature measurement. A short, intensive first pulse is generated through rapid switch-on of the pump source, in the range of faster than 350 ns, preferably faster than 200 ns, in particular preferably faster than 100 ns, quite particularly preferably faster than 50 ns, in particular faster than 10 ns, preferably also from 50 ns to 350 ns. The absence of a radiation field in the resonator results initially in the excessive build-up of a population inversion, which disintegrates abruptly again after the subsequent setting of a radiation field in the resonator (starting operation), wherein the short, intensive first pulse is produced. This laser pulse preferably has a pulse energy of more than 10 µJ, particularly preferably more than 17 µJ. The selected spot diameter of the laser beam can preferably be used to set the power density of the radiation reaching the tissue. The spot diameter can preferably be set from 20 µm to 8.0 mm, particularly preferably from 50 µm to 1.0 mm and, particularly preferably, it is 70 µm. In the case of a spot diameter of 70 µm and a laser power peak of 35 W, a first pulse having a pulse duration of approximately FWHM=0.25 µs results in therapeutic bubble formation in the tissue. In the case of larger spot diameters of, preferably, 0.5 mm and/or lesser laser power peaks such as, for example, 20 W, the pulse is preferably suitable as a measuring pulse.

The rise time E is preferably measured from the instant at which the pump source is switched off, i.e. preferably when the control means supplies a current less than the threshold current, particularly preferably supplies a current of 0 A and a voltage of 0 V to the pump source, to the instant at which the control means supplies the current and the voltage that represent a power corresponding to the pump power level S1. Preferably, the control means generates a current switch-on pulse, whose rising edge attains the current value for the desired pump power level within the rise time E. Preferably, the rise time E lies in the range of at most 300 ns, preferably at most 250 ns, particularly preferably at most 200 ns, quite particularly preferably 150 ns, in particular preferably less than 100 ns. Preferably, following expiry of the rise time E, the pump source is switched off again. It has been found, unexpectedly, that the pulse peak power of the laser pulse rises when the rise time E is reduced. The pulse duration of approximately FWHM=0.25 µs remains substantially constant in this case. Preferably, through the selection of the laser material, it is set to the value defined by the spiking frequency of the selected laser material.

The pump power level S1 is preferably higher than the pump power level S3, to which the pump source can be set for delivery of the CW laser power.

Preferably, the modulation of the laser is based exclusively on the control of the current of the pump diodes of the solid-state laser, and the laser therapy device preferably does not have any additional internal and/or external modulators.

In a further embodiment example according to the invention, the pump power level S1 is at least 10% higher than a pump power level S3, to which the pump source (2) can be set for delivery of the CW laser power of the laser (1).

The pump power level to which the pump source can be set for delivery of the CW laser power of the laser in CW operation is preferably the pump power level required for delivery of the CW nominal power of the laser.

Preferably, the pump power level S1 is 100% to 150%, particularly preferably 110% to 130%, quite particularly preferably 120% of the pump power level to which the pump source can be set as a maximum for delivery of the CW laser power in CW operation. If, for the purpose of generating a first pulse, for example in normal CW operation of the laser, a current of maximally 28 A is supplied to the pump diodes, a current of 33 A is set for the power level N1 with the corresponding voltage, corresponding to an increase to approximately 118%.

In this way, the laser can be briefly excited with a pump power above the pump power stipulated for CW operation, thereby enabling the pulse peak power of a first pulse to be increased again. The brief super-elevation of the excitation power, or pump power, does not result in any damage to the laser itself.

In a further embodiment example according to the invention, the control means (3) is designed to hold the pump source (2) at a pump power level S2 for a time period T after the rise time E.

In this way, it is possible to generate first pulses having a shoulder-type extension after a peak (extended first pulses). Preferably, the time period T directly follows the rise time E. The pump power level S2 is preferably equal to the pump power level S1, particularly preferably equal to the pump power level S3, i.e. approximately equal to a pump power level corresponding to the usual CW nominal power of the laser.

As a result of the excitation power being held at a pump power level S2, additional energy can be introduced into the first pulse, in the form of the trailing shoulder. Therefore, in certain application scenarios, in which the pulse energy of the non-extended first pulse is insufficient to achieve the desired therapeutic effect, the still absent pulse energy can be delivered into the target tissue by means of such after-pumping, after the first pulse.

The time period T is set to a maximum value, such that the sum of the pulse durations of the first pulse and T is preferably less than or equal to 1 ms, particularly preferably less than or equal to 50 µs, quite particularly preferably less than or equal to 10 µs and, in particular preferably, less than or equal to 5 µs. If the extended first pulse has a duration beyond approximately 10 µs to 50 µs, coagulation effects may occur in the tissue, e.g. as a result of heat diffusion, these effects being undesirable in therapy methods that use short, intensive pulses. In an example in which the first pulse has a pulse duration of 200 ns, the time period T is set to a maximum value of, particularly preferably, 4.8 µs, so as to reliably preclude unwanted tissue coagulation effects.

In a further embodiment example according to the invention, a laser pulse energy of the first pulse can be set through the rise time E and/or the time period T and/or the pump power levels S1 and/or S2.

Preferably, the current intensity and/or the rapidity of switch-on, or steepness of the rising edge, which can be set through the time period E, can therefore be used to set the pulse peak power of the first pulse. The time period T, during which a certain pump power level of the pump source is additionally held after the rapid switch-on, can preferably be used to set the additional energy supplied to the pulse by after-pumping.

The invention thereby provides a CW solid-state laser that can be controlled over a wide parameter field and whose laser power peaks and pulse energies can be set within large value ranges (e.g. 0-100 W, preferably 0-50 W, particularly preferably 0-35 W; 0-80 µJ, preferably 0-50 µJ, particularly preferably 0-17 µJ). Hitherto, in the state of the art, in CW operation it has only been possible to generate low power peaks suitable as measuring pulses.

In a further embodiment example according to the invention, the control means (3) is additionally designed to control the pump source (2) in such a manner that a treatment beam having a laser power that is less than or equal to the CW laser power of the laser (1) can be generated by the laser (1) in a continuous operation, and/or treatment pulses having a mean laser power that is less than or equal to the CW laser power of the laser (1) can be generated by the laser (1) in a quasi-continuous operation, and/or measuring pulses and treatment pulses can be generated by the laser (1) in a temperature-regulated, quasi-continuous operation.

For the purpose of generating a treatment beam or treatment pulses, a rise time of the pump source can preferably be set to the pump power level required for this, in the range of from, preferably, 10 µs-2 ms, particularly preferably 10 µs-50 ms. The decay times of a treatment pulse, or treatment beam, can also preferably be set to values in these ranges.

Continuous operation with a treatment beam makes it possible to perform, for example, power-controlled and time-controlled photothermal laser therapy.

By means of a quasi-continuous operation with treatment pulses it is possible to perform, for example, pulsed hyperthermia, or biostimulation.

In a temperature-regulated, quasi-continuous operation with measuring and treatment pulses it is possible to perform, preferably, a temperature-controlled photothermal laser therapy, in particular:

A temperature-controlled photocoagulation with ophthalmoscopically visible lesion of reproducible size, A temperature-controlled photocoagulation with lesion of reproducible size that is ophthalmoscopically invisible but visible in the fluorescence angiogram (ICG angiogram), A temperature-controlled photocoagulation with lesion of reproducible size that is ophthalmoscopically invisible and also invisible in the fluorescence angiogram (ICG angiogram), A temperature-controlled short-pulse photocoagulation (d=100 µs-20 ms), wherein, in particular, the parameter set can be selected so as to be reproducible, such that the lesion is ophthalmoscopically visible at the time of treatment and for a short time thereafter, and becomes ophthalmoscopically invisible from approximately 3 months after the treatment (reversible photocoagulation). The method described here in this case does not have the disadvantage of all previous short-pulse techniques, which, owing to the ever-decreasing therapeutic window, of less than 20 ms of pulse duration, increasingly run the risk of producing uncontrolled vessel ruptures and tissue ruptures (e.g. described in G. Dorin "The treatment of diabetic retinopathy: laser surgery or laser therapy?" Retina Today 6(1) 2008).

A continuous, temperature-controlled hyperthermia that, by means of a temperature that can be set on the retina in a reproducible manner irrespective of individual "extraneous losses" such as, for example, absorption and scattering in the front ocular media and in the inner part of the retina, achieves substantially better clinical results, owing to the uniformity and reproducibility of the thermal action on the retina, even without micropulse methods.

A continuous, temperature-controlled biostimulation, in which thermal activation energies, or steady thermal states (e.g. vascular endothelial growth factor, VEGF, versus pigment epithelium derived factor, PEDF) can be set in a reproducible manner, or displaced in a controlled manner. It is thus possible, for example, to reduce an endogenous expression of VEGF and other angiogenic growth factors.

Whereas, in the state of the art, laser-pump-source switch-on rise times of from 1 µs-10 µs were selected for a measuring pulse, the invention provides for the setting of a greater range of possible rise times, namely, from 0.1-10 µs. In the case of short switch-on times, the pump power level to which the pump source is switched on is preferably reduced accordingly, such that a laser pulse peak power of approximately 10 W is not exceeded.

Preferably, in order to optimize the falling edge of the measuring pulse for the optoacoustic effect, the pump power is regulated briefly after being switched on, e.g. for approximately 2 µs below the subsequent pump power level for delivering the CW laser power (e.g. under the pump power level necessary for photocoagulation). In order to prevent time-wise interference between the optoacoustic pressure transients of the measuring pulse and of the therapy pulse, a pause is preferably inserted between the two pulses, which is preferably greater than the sound propagation time in the eye, e.g. 30 µs. Preferably, measuring and treatment pulses are repeated alternately, at a repetition rate in the range of from 500 Hz-10 kHz, particularly preferably 1 kHz. In a further embodiment according to the invention, however, it is also provided that the therapy pulse follows the measuring pulse directly without a pause. Owing to the absence of a therapy-pulse rising edge, the optoacoustic effect of the therapy pulse can thus be avoided entirely.

Preferably, it is possible to set treatment-pulse rise and fall times that are as long as possible, preferably in the range of from 10 µs-50 µs, such that they do not generate any optoacoustic pressure transients, or generate only a least possible pressure transient.

In an example of a temperature-regulated, quasi-continuous operation with a repetition frequency of 1 kHz (period 1000 µs), a modulation cycle is preferably obtained in the following sequence:

100 µs pump-source off time (extinction time of the radiation field, and disintegration of inversion)

pump-source switch-on for approximately 1 µs (starting operation of the first pulse)

0.5 µs pulse duration of first pulse

0 µs re-adjustment time of rear pulse edge (reduced pump power)

approximately 870 µs "irradiation" time with a continuous pump power for <2.5 W laser output power and rise/fall times each of <50 µs.

The cycle then recommences with a 100 µs pump-source off time, and the other steps are also repeated until, for example, a switch-off criterion, determined by the produced photocoagulation, is attained.

The parameter field specified here as an example makes it possible to realize, for example, a quasi-continuous operation regime by means of the laser therapy device.

In this example of the quasi-continuous operation regime of a CW laser according to the invention, the effective CW irradiation time would only be approximately 13% shorter (i.e.: for the same thermal effect, the CW laser working in quasi-continuous operation has to "heat" for 13% longer than that working in continuous operation). However, it has the advantage of temperature-regulated coagulation without an additional, stronger CW laser or the integration of an additional measuring laser.

A measuring pulse preferably has pulse energies of approximately 2-12 µJ, pulse durations of approximately FWHM=0.25 µs and steep start and end edges.

The described principle according to the invention can preferably also be applied, in a slightly modified form, in a multi-wavelength laser system. In the event that, because of their physical principle of operation, not all installed beam sources are able to simultaneously generate, through the described form of control, a laser signal that can be used for optoacoustic excitation and for temperature-controlled photothermal therapy, a first beam source may preferably be provided to generate the form of laser modulation (measuring pulse and coagulation pulse) described above, and all further beam sources may be used for conventional temperature-controlled photothermal therapy. The first beam source can thus be operated both in a measuring and therapy regime (generation of measuring pulse and therapy pulse) and in a purely measuring regime (generation of measuring pulse only), in which the measuring pulse is generated, while the further beam source can be operated, with a different wavelength, exclusively in a therapy regime. Preferably, in this case, the measuring regime of the first beam source is in the parameter field described above, and both the measuring regime of the first beam source and the therapy regime of the further beam source are each controlled by the same control means. Consequently, likewise, it is possible to dispense with the additional beam source for generating the measuring pulse.

An aspect of the invention is also achieved in this special case of the multi-wavelength laser system, since it is possible to dispense with the additional beam source for generating the measuring pulse. Preferably, the laser therapy device has at least two lasers, wherein at least one of the lasers provides at least one wavelength that can be used for at least two of the operating modes: first-pulse operation, continuous operation, quasi-continuous operation and temperature-regulated, quasi-continuous operation.

In a further embodiment example according to the invention, the control means (3) is additionally designed to control the pump source (2) in respect of time in such a manner that first pulses and/or treatment pulses and/or measuring pulses, or a combination of first pulses and/or treatment pulses and/or measuring pulses, can be generated as pulse packets.

A pulse packet consists of at least two pulses, between which there is a pause that is shorter than a pause before another pulse packet.

The combination of various pulses, or pulse packets, makes it possible, preferably, to set a great variety of measuring and therapy scenarios. For example, a combination of exclusively first pulses, both as single pulses and as pulse packets, makes it possible to perform selective hyperthermia of the trabecular meshwork, which results in a reduction of the intraocular pressure. Moreover, the combination of exclusively extended first pulses, both as single pulses and as pulse packets, in the range of from 250 ns-5 µs, makes it possible to perform a selective photothermolysis/hyperthermia of the trabecular meshwork for the purpose of reducing the intraocular pressure. A combination of first pulses, as single pulses or, also, as a pulse packet, and also the combination of extended first pulses, both as single pulses and, also, as pulse packets, in the range of from 250 ns-5 µs, makes it possible to perform, preferably, a selective photothermolysis, in which cells of the RPE die off as a result of bubble formation. The combination of measuring pulses and treatment pulses makes it possible, for example, to perform a temperature-regulated photothermal laser therapy that can be performed as hyperthermia and biostimulation in the case of below-threshold power values of the treatment pulse, and as irreversible or reversible photocoagulation in the case of above-threshold power values of the laser pulse.

The laser therapy system according to the invention described above can be used within known application systems such as, for example, an ophthalmological laser slit lamp, a link system for conventional ophthalmological biomicroscopes, fundus camera systems or, also, OCT systems. It is provided in this case that the therapeutic spot size can be set from approximately 10 µm to approximately 1 mm. Also provided, in addition to the manually settable application of the laser spot in the eye, is an automated, or also partially automated, application of the laser spot by means of an optical scanning system. Line scans are provided in this case, as well as flat grating scans, which allow efficient working. Preferably, the spatial form and arrangement of the therapeutic laser spot can be configured in such a manner that the spot size can be set by an optical system, and the arrangement of a multiplicity of spots is effected by a manual and/or automatic optical positioning or scanning system.

Particularly in the case of work with below-threshold, and therefore not ophthalmoscopically visible, laser effects, registering of the sites of action of the laser radiation in the eye is provided in the application system. Preferably in this case, optical image processing methods are used, which register on salient features of the eye such as, for example, the macula, the optic nerve or blood vessels.

Particularly for first-pulse operation, extended first-pulse operation and quasi-continuous pulse operation for performing selective photothermolysis, it is provided that the spot size is set in dependence on the pulse length and pulse energy so as to achieve selective photodisruption (bubble formation) in the RPE.

An aspect of the invention is furthermore achieved, in particular, by a method for operating a laser therapy device (4), comprising the following step:
  generating at least one first pulse (2) of a laser (1), which is a solid-state laser suitable for a CW operation, by switching on a pump source (2), by means of a control means (3), to a pump power level S1, wherein the switch-on is effected within a rise time E in the range of from 50 ns to 350 ns, after which the pump power level S1 of the pump source (2) is attained, starting from the switch-on.

In a further method according to the invention, the pump power level S1 is at least 10% higher than a pump power level S3, to which the pump source (2) is set for delivery of the CW laser power of the laser (1).

A further method according to the invention additionally comprises the step:
  setting the pump source (2) to a pump power level S2, which is maintained for a time period T after the rise time E.

A further method according to the invention additionally comprises the step:
  setting a laser pulse energy of the first pulse in dependence on the time period E and/or on the time period T and/or on the pump power levels S1 and/or S2.

A further method according to the invention additionally comprises at least one of the steps:
  generating a treatment beam of the laser (1) in a continuous operation with a laser power that is less than or equal to the CW laser power of the laser (1);

generating treatment pulses of the laser (1) in a quasi-continuous operation, which have a mean laser power that is less than or equal to the CW laser power of the laser (1);

generating measuring pulses and treatment pulses of the laser (1) in a temperature-regulated, quasi-continuous operation.

A further method according to the invention additionally comprises the step:

generating pulse packets of first pulses and/or treatment pulses and/or measuring pulses, or a combination of first pulses and/or treatment pulses and/or measuring pulses.

Figure 2:
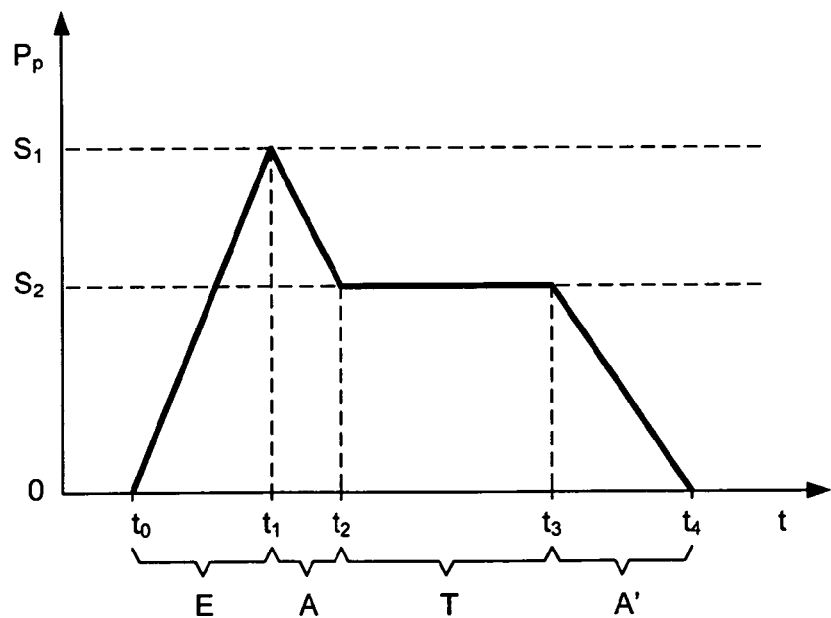
Figure 3:
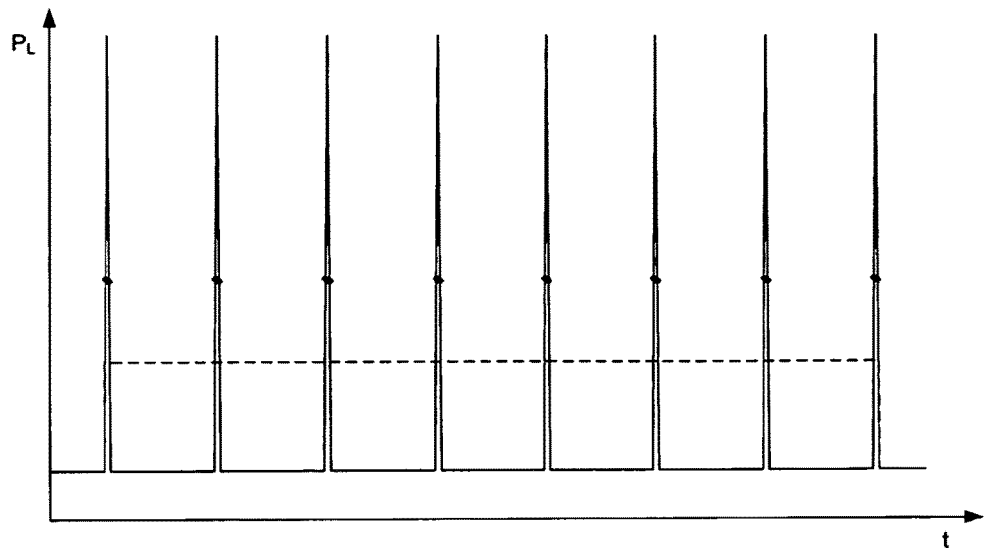
Figure 4:
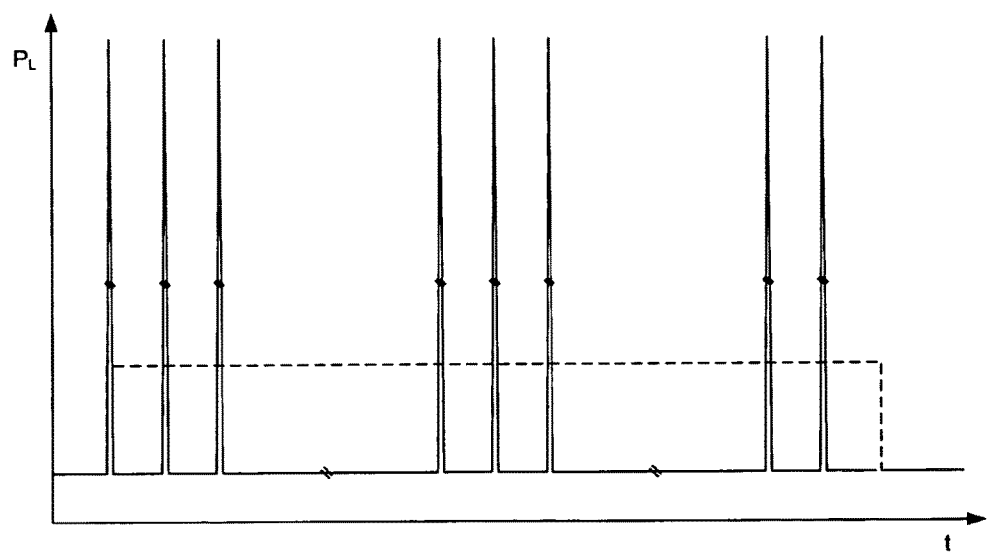
Figure 5:
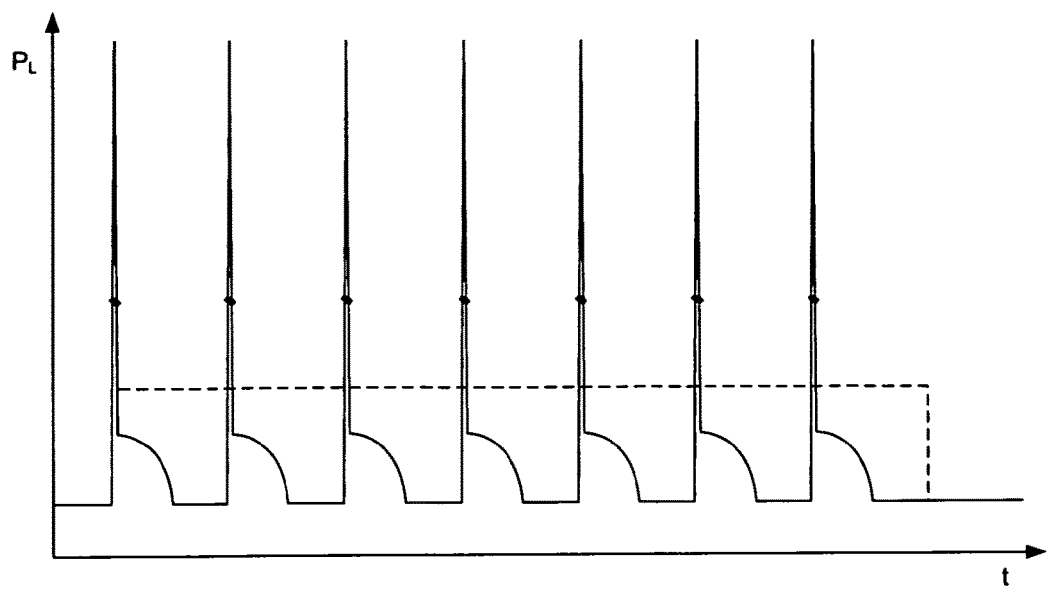
Figure 6:
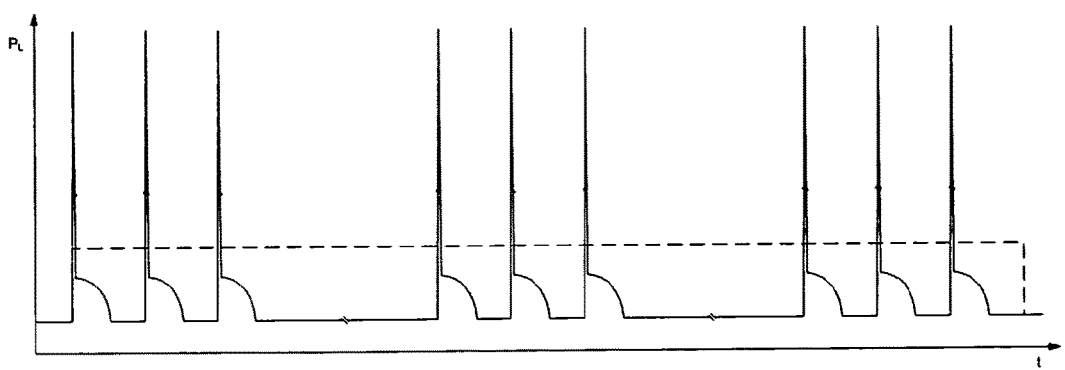
Figure 7:
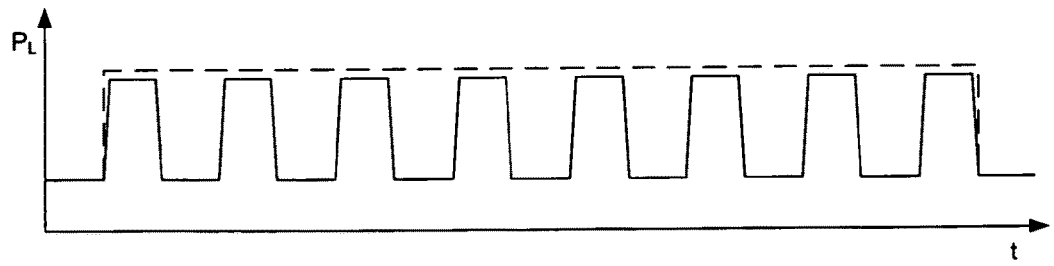
Figure 8:
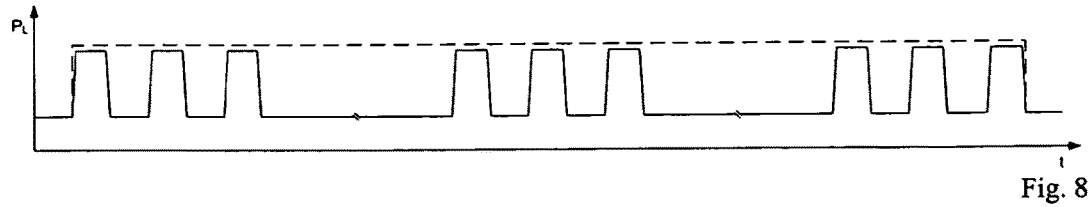
Figure 9:
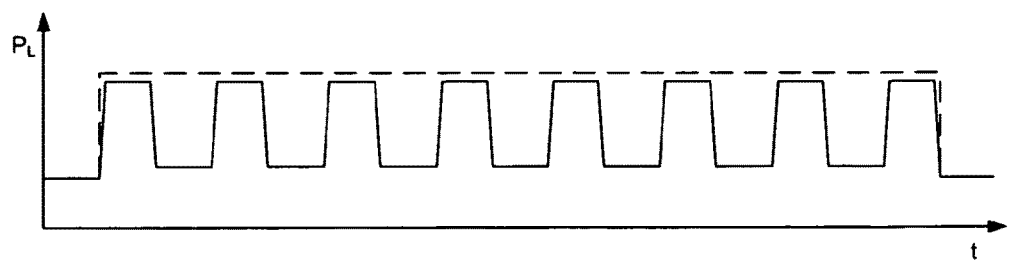
Figure 10:
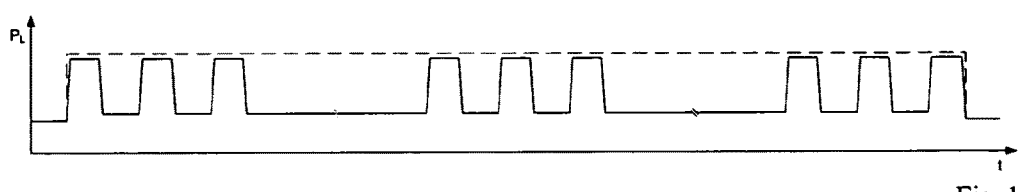
Figure 11:
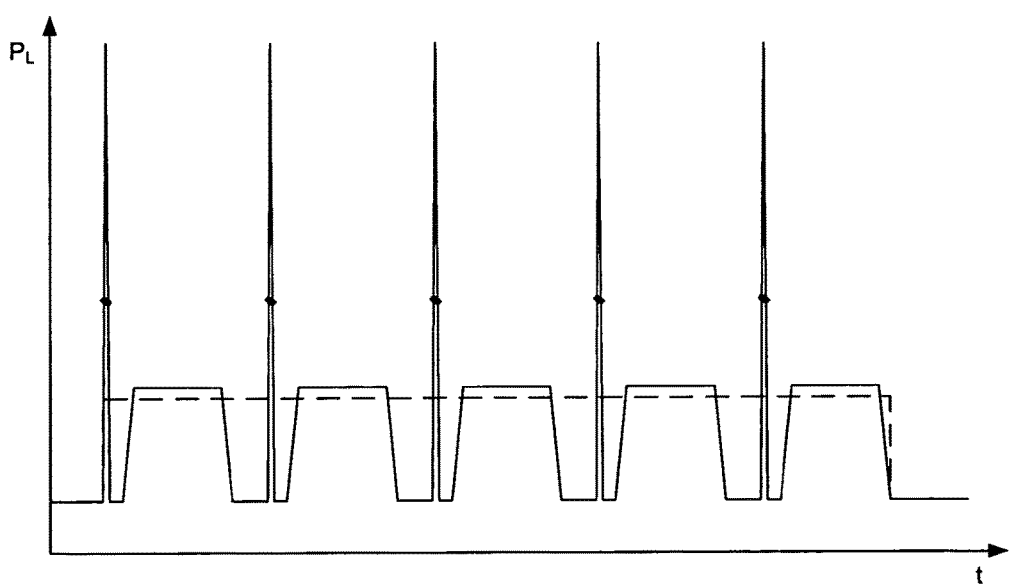
Figure 12:
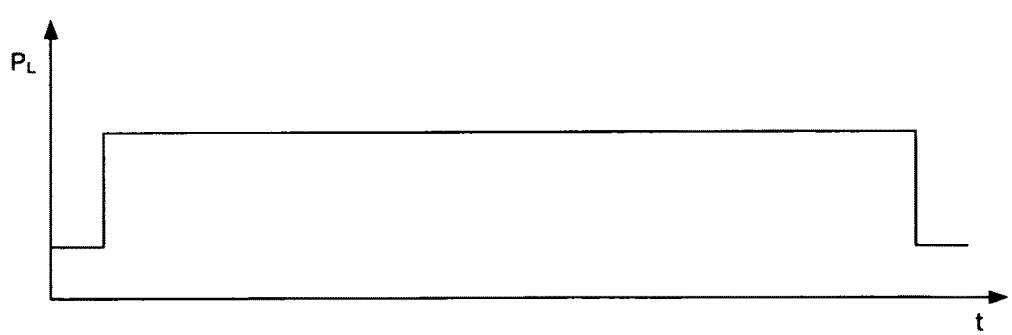

FIG. 1 an overview of a laser therapy device (4) according to the invention,

FIG. 2 a pump power (PP)-time (t) diagram of a control, according to the invention, of a pump source (2), FIG. 3 a laser power (PL)-time (t) diagram of first pulses according to the invention, FIG. 4 a laser power (PL)-time (t) diagram of pulse packets of first pulses according to the invention, FIG. 5 a laser power (PL)-time (t) diagram of extended first pulses according to the invention, with a shoulder characteristic resulting from holding a pump power level S2 after switch-on of the pump source to a pump power level S1, FIG. 6 a laser power (PL)-time (t) diagram of pulse packets of extended first pulses according to the invention, with a shoulder characteristic, FIG. 7 a laser power (PL)-time (t) diagram of treatment pulses according to the invention and of a treatment beam according to the invention, FIG. 8 a laser power (PL)-time (t) diagram of pulse packets of treatment pulses according to the invention, FIG. 9 a laser power (PL)-time (t) diagram of treatment pulses according to the invention without complete reduction of the pump power between the treatment pulses, FIG. 10 a laser power (PL)-time (t) diagram of pulse packets of treatment pulses according to the invention without complete reduction of the pump power between the treatment pulses, FIG. 11 a laser power (PL)-time (t) diagram of treatment pulses and measuring pulses according to the invention, FIG. 12 a laser power (PL)-time (t) diagram of a CW treatment beam according to the invention.

FIG. 1 shows an overview of a laser therapy device 4 according to the invention. The laser 1 is connected to a pump source 2, which excites the laser. The control unit 3 is connected to the pump source 2, and is designed to control the pump source 2. Optionally, the laser, in its output, has an optical waveguide (not shown), which directs the laser light further on to an eye, via a slit lamp (not shown).

When the invention is in operation, the control means 3 controls the pump source 2 by a rapid switch-on, with a rise time of approximately 100 ns, to a pump power level S1. In this case, a current of 33 A is delivered by the control unit 3 to the pump source 2. In response to this abrupt switch-on of the pump source 2, there is an excessive build-up of the population inversion in the laser medium, which disintegrates abruptly again after the subsequent setting of a radiation field in the laser resonator, and wherein a short, intensive pulse (first pulse) is produced. In the case of a CW laser power of approximately 2 W, this laser pulse attains power peak values of approximately 35 W, and is therefore suitable for producing therapeutic effects in the tissue.

In this way, the laser power is increased briefly by a multiple of the CW laser power, approximately by a factor of 10-17. For example, a first pulse having a pulse peak power of approximately 50 W can be generated in this way with a CW laser having a CW laser power of approximately 5 W. As a result, a multiplicity of new application possibilities are created for this laser, substantially reducing the amount of equipment required, e.g. in a clinic.

FIG. 2 shows a pump power (PP)-time (t) diagram of a control, according to the invention, of a pump source (2). In this example, a first pulse is generated by the control operation. The pump source 2 is switched on at an instant T0, and is powered-up to a pump power level S1, up to an instant T1. This difference T1-T0 then corresponds to the rise time E, which in this example is 100 ns. The pump power is then powered-down to a pump power level S2, at which it is held from T2 to T3, wherein T3-T2=T. The pump power is then reduced back to 0, up to a point T4. The decay times A and A', in the case of short decay times, are preferably negligible relative to the time period T. Preferably, however, these decay times are also calculated into the time period T, such that, contrary to the representation shown here, T=T4-T1. Preferably, the same value as that of the pump power level S1 can be set as a pump power level S2. There is therefore no decay time A.

In this way, an extended first pulse, having a shoulder characteristic of the laser 1, can be generated. By means of the parameters T, S1 and S2, wherein the decay times A and A' are preferably also included in T, it is possible to set the maximum laser pulse power and the total pulse energy carried in the extended first pulse.

FIG. 3 shows a laser power (PL)-time (t) diagram of first pulses according to the invention. Additionally indicated, by a broken line (as also in FIGS. 4-11 that follow), is the CW laser power that the laser seeks to deliver when in a continuous laser operation. In this example, the pump source is also switched off again as rapidly as possible after attaining the pump power level S1, such that no shoulder characteristic of the laser power is produced after the respective pulse. Between the pulses, pauses of more than 100 µs are maintained, in which the pump source 2 remains switched off and in which the radiation field present in the laser resonator is extinguished and a residual population inversion degenerates through spontaneous disintegration.

In this way, a CW laser can be used to perform, for example, a selective photothermolysis, which, in the state of the art, is possible only by means of short-pulsed diode lasers that are specially suited to this purpose, but in which, owing to the absence of an ophthalmoscopically visible clinical end point, the correct dosing of the laser energy can then only be adapted empirically, starting from an overdosed, visible lesion, by reduction of the laser power.

FIG. 4 shows a laser power (PL)-time (t) diagram of pulse packets of first pulses according to the invention. Between the pulse packets, which in this case consist of three first pulses, longer pauses are maintained than between the single pulses of a pulse packet. Owing to the long pauses between the pulse packets, the mean laser power can be reduced considerably, if necessary, while maintaining the pulse waveforms of the single pulses.

FIG. 5 shows a laser power (PL)-time (t) diagram of first pulses according to the invention with a shoulder characteristic that results from a pump power level S2 being maintained after the pump source has been switched on to a pump power level S1. This results in a shoulder being produced behind each first pulse, the shoulder then decaying again relatively rapidly, since the pump source is then switched off again sufficiently early, such that no thermal coagulation occurs.

It is thus possible to generate single pulses having a high pulse peak power of the laser pulses and a high total pulse energy. This is particularly advantageous for many therapeutic applications such as, for example, selective photothermolysis, which may be used, for example, in selective retinal therapy (SRT) of the RPE in the case of diabetic maculopathy or in the case of drusen in age-related macular degeneration.

FIG. 6 shows a laser power (PL)-time (t) diagram of pulse packets of first pulses according to the invention, with a shoulder characteristic. In this example, the shoulders of the individual first pulses are each below the laser power level that would be emitted by the laser in continuous operation. It is thus possible to generate pulse packets with single pulses having a high pulse peak power and a high total pulse energy. Again, as in FIG. 4, the long pauses between the pulse packets enable the mean power to be reduced. This is particularly advantageous for many therapeutic applications such as, for example, selective photothermolysis, which may be used, for example, in the case of selective retinal therapy (SRT) of the RPE in the case of diabetic maculopathy or in the case of drusen in age-related macular degeneration.

FIG. 7 shows a laser power (PL)-time (t) diagram of treatment pulses according to the invention and of a treatment beam according to the invention. The treatment pulses have a pulse peak power that corresponds to the CW laser power. An individual pulse in this case has lengths in the range of from 100 µs-200 µs, in this case 200 µs. Preferably, between the pulses, pauses are maintained that are shorter than the fluorescence lifetime of the laser medium used, e.g. pauses that are shorter than 100 µs.

In this way the CW laser can be operated in a pulsed manner, e.g. for photocoagulation. Owing to the pauses between the pulses, the mean power can be reduced considerably, if necessary, without influencing the individual pulses.

FIG. 8 shows a laser power(PL)-time (t) diagram of pulse packets of treatment pulses according to the invention. These can be used, for example, for therapy by hyperthermia without coagulation effects. Again, the pauses between pulse packets enable the mean laser power to be reduced.

FIG. 9 shows a laser power(PL)-time (t) diagram of treatment pulses according to the invention without complete reduction of the pump power between the treatment pulses. Between the treatment pulses, the pump power is held at a value of slightly above zero. This prevents pauses between the pulses, in which the upper laser level could decay and in which a first pulse would be produced upon re-excitation.

Consequently, with a rapid rise time, there is a less pronounced over-population of the laser level to which the laser is excited, and there is therefore no sudden laser discharge after a rapid build-up for a treatment pulse. In this way, first pulses are avoided in a yet more reliable manner while rise times of treatment pulses remain the same, and shorter switch-on times can be set for a normal pulse, without the occurrence of a first pulse. Moreover, the mean laser power can be set in a flexible manner, e.g. by means of pulse-width modulation, wherein first pulses are prevented. A laser can thus be operated with a fixed laser power level (e.g. the CW nominal power), while the mean laser power can be set to a multiplicity of intermediate values, according to the pulse length and/or pause length between the power at which the laser is held at values slightly above zero in the pauses and the fixed power level. In the case of conventional photocoagulation lasers, cell death as a result of bubble formation almost always occurs at a beam diameter of 50 µm or 100 µm. By contrast with this, since the laser power can be set to a multiplicity of intermediate values, and since the first pulses are prevented, hyperthermia, or photocoagulation, can be achieved in a reproducible manner, even in the case of small beam diameters. The laser can thus also be used for those therapies in which healing effects occur as a result of migration of adjacent RPE cells.

FIG. 10 shows a laser power(PL)-time (t) diagram of pulse packets of treatment pulses according to the invention without complete reduction of the pump power between the treatment pulses.

FIG. 11 shows a laser power(PL)-time (t) diagram of treatment pulses and measuring pulses according to the invention. Before a measuring pulse, the pump source is switched off for 75 µs, such that the radiation field in the laser resonator and the existing population inversion disintegrate. The pump source is then switched on for approximately 1 µs, resulting in the maintenance of a pulse peak power of the laser pulse of approximately 10 W. This pulse is used as a measuring pulse for the temperature of the tissue to be treated. The pump power is then reduced, for approximately 30 µs, to a pump power level at which no thermal effects occur in the tissue. A treatment pulse is then generated for approximately 780 µs, this treatment pulse, however, having a laser power value of slightly above the CW nominal power, as a result of the pump power level of the pump source having been set accordingly, such that the treatment pulses have, on average, a pulse energy that is also the energy of a continuous treatment beam in continuous operation of the laser, in which the stipulated mean CW laser power of the laser is set. The rise and decay times of the treatment pulses are approximately 40 µs.

FIG. 12 shows a laser power(PL)-time (t) diagram of a CW treatment beam according to the invention.

This invention presents modulation methods for a conventional CW laser that greatly extend the spectrum of application of a CW laser, e.g. in the clinical field, in comparison with the state of the art. In particular, by means of a first-pulse operation, the laser can generate pulse peak powers previously considered not possible for a CW laser. The pulse peak power in this case is increased, by more than 10 times the mean power level of the CW laser, through special control of the laser by a pump source. As a result, forms of therapy such as, for example, selective photothermolysis in the retinal pigment epithelium (RPE), become possible with a CW laser for the first time. This increase in power is effected through rapid switch-on of the pump source, in the range of from 50-350 ns. The diversity of application of a CW laser is also enhanced by the step of a method according to the invention, or a control means designed to execute this step, in which, in addition to the rapid switch-on of the pump source, after-pumping is also continued for a certain time T, and a first pulse can thus be set to a multiplicity of laser power settings. In addition, the laser therapy device has further modulation possibilities, which enable e.g. a quasi-continuous operation or an operation in which a temperature-controlled, quasi-continuous treatment by means of measuring pulses and treatment pulses is possible. The invention thus provides an apparatus and a method in which, with a single laser resonator and merely through selective electrical control of the pump diodes, both coagulation of tissue is achieved, in continuous laser operation, and temperature-regulated laser coagulation, or laser therapy of the retina, is effected, in quasi-continuous operation and, furthermore within a first-pulse operating mode, a selective photothermolysis of the retinal pigment epithelium (RPE) is achieved without thermal damage to the photoreceptors (PR) or to the choroid membrane.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

REFERENCES 1 laser
2 pump source
3 control means
4 laser therapy device

What is claimed is:

1. A laser therapy device comprising:
a solid-state laser suitable for continuous-wave (CW) operation;
a pump source configured to excite the laser; and
a controller configured to increase, during a rise time E, a pump power supplied to the pump source from a minimum pump power level to a maximum pump power level S1 thereby generating a first pulse of the laser,
wherein the rise time E is in a range of from 50 ns to 350 ns.

2. The laser therapy device recited in claim 1, wherein the maximum pump power level S1 is at least 10% higher than a pump power level S3 that can be supplied to the pump source so as to generate a CW laser power of the laser.

3. The laser therapy device recited in claim 1, wherein the controller is further configured to reduce the pump power supplied to the pump source to a pump power level S2 and hold the pump power supplied to the pump source at the pump power level S2 for a time period T after the rise time E.

4. The laser therapy device recited in claim 3, wherein a laser pulse energy of the first pulse of the laser is settable through at least one of the rise time E, the time period T, the pump power level S1, or the pump power level S2.

5. The laser therapy device recited in claim 1, wherein the controller is further configured to control the pump source so as to carry out at least one of:
generating, in a continuous operation of the laser, a treatment beam having a laser power that is less than or equal to a maximum possible CW laser power of the laser,
generating, in a quasi-continuous operation of the laser, treatment pulses having a mean laser power that is less than or equal to the CW laser power of the laser, or
generating, in a temperature-regulated quasi-continuous operation of the laser, measuring pulses and treatment pulses.

6. The laser therapy device recited in claim 1, wherein the controller is configured to control the pump source with respect to time in such a manner that at least one of additional first pulses, treatment pulses having a power equal to or less than the first pulses, measuring pulses having a lower power than the treatment pulses, or a combination thereof, are generated as pulse packets.

7. The laser therapy device recited in claim 1, wherein the first pulse of the laser has a first pulse peak power that is more than 10 times greater than a CW power of the CW operation of the laser.

8. The laser therapy device recited in claim 1, wherein the laser has a wavelength ranging from 400 nm to 1064 nm.

9. The laser therapy device recited in claim 1, wherein the solid-state laser suitable for CW operation is configured to provide a CW laser power of up to 5 W.

10. The laser therapy device recited in claim 1, wherein the solid-state laser suitable for CW operation is a primarily continuously emitting therapy laser configured to provide a CW laser power of 100 mW to 500 mW for coagulation times of 10 ms to 500 ms.

11. The laser therapy device recited in claim 10, wherein the solid state laser suitable for CW operation has a wavelength ranging from 400 nm to 1000 nm.

12. The laser therapy device recited in claim 11, wherein the solid state laser suitable for CW operation has a wavelength ranging from 510 nm to 810 nm.

13. The laser therapy device recited in claim 12, wherein the solid state laser suitable for CW operation has a wavelength of 532 nm, 561 nm, 577 nm, or 659 nm.

14. The laser therapy device recited in claim 1, wherein the minimum pump power level is a pump power level that is supplied when the pump source is turned off.

15. The laser therapy device recited in claim 1, wherein the minimum pump power level is 0 W.

16. The laser therapy device recited in claim 1, wherein the controller is further configured to, after the rise time E, iteratively reduce the pump power supplied to the pump source to the minimum power level, maintain the minimum power level supplied to the pump source for a pause time, and then increase the pump power level supplied to the pump source from the minimum pump power level to maximum pump power level S1 during the rise time E thereby generating one or more additional first pulses of the laser.

17. The laser therapy device recited in claim 16, wherein the pause time is from 40 μs to 2 ms.

18. The laser therapy device recited in claim 16, wherein the pause time is equal to an upper-state lifetime of the laser.

19. The laser therapy device recited in claim 16, wherein the minimum pump power level is 0 W.

20. A method for operating a laser therapy device, the method comprising:
- increasing, from a minimum pump power level to a maximum pump power level S1 during a rise time E, a pump power supplied to a pump source configured to excite a solid-state laser thereby generating a first pulse of the laser,
- wherein the rise time E is in a range of from 50 ns to 350 ns, and
- wherein the laser is suitable for a continuous-wave (CW) operation.

21. The method recited in claim 20, wherein the pump power level S1 is at least 10% higher than a pump power level S3 to which the pump source is set so as to generate a CW laser power of the laser.

22. The method recited in claim 20, further comprising:
- reducing the pump power supplied to the pump source to a pump power level S2; and
- maintaining the supply of the pump power to the pump source with the pump power level S2 for a time period T after the rise time E.

23. The method recited in claim 22, further comprising:
- setting a laser pulse energy of the first pulse of the laser in dependence on at least one of the rise time E, the time period T, the pump power level S1, or the pump power level S2.

24. The method recited in claim 20, further comprising at least one of:
- generating, by the laser in a continuous operation, a treatment beam with a laser power that is less than or equal to a maximum possible CW laser power of the laser
- generating, by the laser in a quasi-continuous operation, treatment pulses that have a mean laser power that is less than or equal to the CW laser power of the laser; or
- generating, by the laser in a temperature-regulated, quasi-continuous operation, measuring pulses and treatment pulses.

25. The method recited in claim 20, further comprising:
- generating pulse packets of at least one of additional first pulses, treatment pulses having a power equal to or less than the first pulses, measuring pulses having a lower power than the treatment pulses, or a combination thereof.

* * * * *